United States Patent
Ma

(10) Patent No.: US 10,053,278 B2
(45) Date of Patent: Aug. 21, 2018

(54) READILY MANUALLY ACCESSIBLE DISPOSABLE GLOVES

(71) Applicant: Richard Ma, Carlisle, MA (US)

(72) Inventor: Richard Ma, Carlisle, MA (US)

( * ) Notice: Subject to any disclaimer, the term of this patent is extended or adjusted under 35 U.S.C. 154(b) by 0 days.

(21) Appl. No.: 15/403,911

(22) Filed: Jan. 11, 2017

(65) Prior Publication Data

US 2018/0194539 A1    Jul. 12, 2018

(51) Int. Cl.
*B65D 83/08* (2006.01)
*A41D 19/00* (2006.01)
*B65D 83/00* (2006.01)

(52) U.S. Cl.
CPC ......... *B65D 83/08* (2013.01); *A41D 19/0072* (2013.01); *A41D 19/0082* (2013.01); *B65D 83/0088* (2013.01); *A41D 2400/52* (2013.01); *A41D 2500/20* (2013.01); *A41D 2500/40* (2013.01); *A41D 2500/52* (2013.01)

(58) Field of Classification Search
CPC ... A41D 19/0072; A47G 25/904; A61B 42/40
See application file for complete search history.

(56) References Cited

U.S. PATENT DOCUMENTS

| | | | | | |
|---|---|---|---|---|---|
| 3,851,760 | A | * | 12/1974 | Smith | B65D 83/0805 206/278 |
| 4,034,853 | A | * | 7/1977 | Smith | B29C 65/18 156/251 |
| 4,094,120 | A | * | 6/1978 | Goncalves | A41D 19/0068 229/87.16 |
| 4,677,697 | A | * | 7/1987 | Hayes | A41D 19/0068 2/159 |
| 4,773,532 | A | * | 9/1988 | Stephenson | B65D 83/0811 206/278 |
| 6,021,919 | A | * | 2/2000 | Kelly | A61B 42/40 221/155 |
| 6,497,340 | B2 | * | 12/2002 | Grinberg | A41D 19/0072 2/158 |
| 6,637,035 | B1 | * | 10/2003 | Brinkmann | A41D 19/01 15/227 |
| 8,807,402 | B2 | * | 8/2014 | Backhaus | A41D 19/0072 223/111 |
| 2002/0160896 | A1 | * | 10/2002 | Yeh | B65H 35/10 493/180 |
| 2005/0066413 | A1 | * | 3/2005 | Mattesky | A47G 25/904 2/161.6 |

* cited by examiner

*Primary Examiner* — Gene O Crawford
*Assistant Examiner* — Ayodeji T Ojofeitimi
(74) *Attorney, Agent, or Firm* — Polsinelli, PC

(57) ABSTRACT

Apparatus and method for enabling serial delivery of a plurality of interconnected gloves, the apparatus comprising:
a plurality of flexible gloves,
a distal tip end of one or more of the fingers of a downstream one the plurality of gloves being readily detachably attached to a bottom proximal edge of an open bottom end of an immediately upstream one of the plurality gloves.

16 Claims, 12 Drawing Sheets

READILY MANUALLY ACCESSIBLE DISPOSABLE GLOVES

BACKGROUND

Disposable gloves are commonly used by doctors, nurses and health care providers generally when examining patients. The health care provider typically uses the gloves to as sterile a contact with some portion of the surface of the patient.

SUMMARY OF INVENTION

In accordance with the invention there is provided an apparatus 5 enabling serial delivery of a plurality of interconnected gloves 10, the apparatus comprising:

a plurality of flexible gloves 10, each flexible glove comprised of a top 50 and a bottom 60 sheet of polymeric material, the top and bottom sheets being sealably attached to each other in an arrangement that forms five enclosed fingers, TR, IR, MR, RR, LR, adapted to generally receive five fingers of a human hand, and an enclosed palm portion 10p having an open bottom end 59o adapted to generally receive a palm of a human hand, a distal tip end 300, 302 of one or more of the fingers IR, MR, RR of a downstream one 10c the plurality of gloves being readily detachably 302p, 304p attached to a bottom proximal edge 57 of an open bottom end 59o of an immediately upstream one 10b of the plurality gloves, the attached upstream 10b and downstream 10c gloves forming a continuum of serially attached gloves formable into a cylinder or roll 20, each of the serially attached gloves having a longitude L generally extending from the distal tip end 304 of the one or more fingers to the open bottom end 59o, the serially attached downstream 10c and upstream 10b ones of the plurality of gloves 20 being readily detachable from each other by exertion of human manual pulling force on one or both of the serially attached gloves wherein the pulling force is exerted in a direction along the longitude L of the serially attached gloves that pulls the serially attached gloves in opposite directions or away from each other.

The tip ends 302p, 304p of at least two of the fingers of the downstream one of the serially attached gloves is readily detachably attached to the bottom proximal edge 57 of the open bottom end 59o of an immediately upstream one of the plurality gloves.

Each of the gloves can have five fingers arranged and configured generally corresponding to the arrangement of a thumb, a forefinger, a middle finger, a ring finger and a pinky finger of a human hand, wherein the tip end of either the forefinger and the middle finger or the middle finger and the ring finger are the only fingers that are readily detachably attached to the bottom proximal edge of the open bottom end of an immediately upstream one of the plurality gloves.

The at least two of the fingers of the downstream one of the serially attached gloves are typically readily detachably attached to the bottom proximal edge 57 of the open bottom end 59o of the immediately upstream one 10b of the plurality gloves in an arrangement that forms an enclosed groove or slot S between opposing edges 302e, 304e of the at least two fingers of the immediately downstream one 10c of the gloves and the bottom proximal edge 57 of the open bottom end 59o of the immediately upstream 10b one of the gloves.

The apparatus can further comprise a dispenser 800 comprising a base 121 and a cylinder 152 mounted on the base 121, the cylinder 152 having an axis A around which the roll 20 of gloves is mounted and is rotatable R, the dispenser including a detent 126 mounted to the base in an arrangement relative to the cylinder wherein a downstreammost glove 10c on the roll 20 is manually graspable by a user to dispose the detent 126 within the slot S with a downstream pulling motion P to forcibly engage the detent 126 against the bottom proximal edge 57 of a glove that is attached immediately upstream 10b to the downstreammost 10c glove.

The downstream and upstream gloves can be readily detachably attached to each other via a series of adjacent perforations 202p, 302p formed in sequential linear or curvilinear arrangement or seam in a sheet of the polymeric material that extends between the distal tip ends of the one or more fingers of the downstream glove and the bottom proximal edge 57 of the open bottom end 59o of the upstream glove, the perforations being formed of a size selected to enable ready detachment along the linear or curvilinear arrangement of perforations by exertion of normal pulling force by human hand.

A plurality of additional gloves 10a et al. are typically readily detachably attached to the upstream and downstream gloves in the same manner that the upstream and downstream gloves are readily detachably attached to each other to form a continuum of at least three serially attached gloves that are formable into a cylinder or roll 20.

The sheet of polymeric material typically comprises a woven or punch formed fabric, a paper material or a solid polymeric material comprised of one or more of polyethylene, polypropylene, polyester or the like and wherein the sheet has a thickness of less than about 500 microns.

In another aspect of the invention there is provided a method of delivering a series of gloves to a user in serial fashion comprising rotatably mounting a roll of interconnected gloves as claimed in claim 1 on a cylinder in an arrangement wherein a downstreammost glove on the roll is readily manually engageable by a user to pull the downstreammost glove apart from an immediately upstream attached glove.

In another aspect of the invention there is provided an apparatus 5 enabling serial delivery of a plurality of interconnected gloves 10, the apparatus comprising:

a plurality of flexible gloves, each flexible glove comprised of a top 50 and a bottom 60 sheet of polymeric material, the top and bottom sheets being sealably attached to each other in an arrangement that forms a first thumb 105 receptacle and at least a second finger receptacle 108 that is adapted to receive at least two other fingers 110, 112, 114 of a human hand, and an enclosed palm portion 10p having an open bottom end 59o adapted to generally receive a palm of a human hand, a distal tip end 67 of the second finger receptacle 108 being readily detachably attached to a bottom proximal edge 57 of an open bottom end 59o of an immediately upstream one 10b of the plurality gloves, the attached upstream 10b and an immediately downstream 10c glove forming a continuum of serially attached gloves formable into a cylinder or roll 20, each of the serially attached gloves 10a, 10b, 10c having a longitude L generally extending from the distal tip end 67 of the second finger 108 receptacle to the open bottom end 59o or edge 57, the serially attached downstream and upstream ones of the plurality of gloves being readily detachable from each other by exertion of human manual pulling force on one or both of the serially attached gloves wherein the pulling force P is exerted in a direction along the longitude L of the serially attached gloves that pulls the serially attached gloves in opposite directions or away from each other.

The second of the at least two finger receptacles is typically adapted to receive at least three fingers 110, 112, 114 of a human hand.

The tip end 67 of the second 108 of the at least two finger receptacles of the downstream one 10*c* of the serially attached gloves is preferably readily detachably attached 30, 32 to the bottom proximal edge 57 of the open bottom end 59*o* of an immediately upstream one of the plurality gloves.

The tip end 67 of the second 108 of the at least two finger receptacles of the downstream one 10*c* of the serially attached gloves is readily detachably attached to the bottom proximal edge 57 of the open bottom end of an immediately upstream one 10*b* of the plurality gloves.

Such an apparatus can further comprise a dispenser 800 comprising a base 121 and a cylinder 45 mounted on the base, the cylinder 45 having an axis A around which the roll 20 of gloves is mounted and is rotatable R such that a downstreammost 10*c* glove on the roll 20 is manually graspable by a user to pull the downstreammost glove 10*c* apart from an immediately upstream attached glove 10*b*.

The downstream and upstream gloves 10*b*, 10*c* are readily detachably attached to each other via a series of adjacent perforations 30 formed in sequential linear or curvilinear arrangement or seam 32 in a sheet of the polymeric material that extends between the distal tip end of the second of the finger receptacles of the downstream glove and the bottom proximal edge of the open bottom end of the upstream glove, the perforations being formed of a size selected to enable ready detachment along the linear or curvilinear arrangement of perforations by exertion of normal pulling force by human hand.

A plurality of additional gloves are typically readily detachably attached to the upstream 10*b* and downstream 10*c* gloves in the same manner that the upstream and downstream gloves are readily detachably attached to form a continuum of at least three serially attached gloves that are formable into a cylinder or roll.

The sheet of polymeric material preferably comprises a woven or punch formed fabric, a paper material or a solid polymeric material comprised of one or more of polyethylene, polypropylene, polyester or the like and wherein the sheet has a thickness of less than about 500 microns.

In another aspect of the invention there is provided a method of delivering a series of gloves to a user in serial fashion comprising rotatably mounting a roll of interconnected gloves as claimed in claim 10 on a cylinder in an arrangement wherein a downstreammost glove on the roll is readily manually engageable by a user to pull the downstreammost glove apart from an immediately upstream attached glove.

In another aspect of the invention there is provided an apparatus 5 enabling serial delivery of a plurality of gloves 10, the apparatus comprising:

a series of gloves mounted in a stack 450 on a mount 500, each individual glove 10 in the stack comprising a top or front thin sheet 50 and a bottom or back thin sheet 60, the top and bottom sheets formed integrally together to form a flexible glove having one or more enclosed finger receptacles TR, IR, MR, RR, LR adapted to receive one or more complementary fingers of a human hand, and an enclosed palm portion 10*p* having an open bottom end 59*o* adapted to generally receive a palm of a human hand, the front and back sheets each having a different front and back longitudinal length L1, L2 respectively extending from a common distal or top edge 304*t* of the longest finger receptacle MR to a proximal or bottom edge 57, 57*p* of each of the front and back sheets of the glove respectively, wherein the longitudinal length of the back sheet L2 is longer than the longitudinal length L1 of the front sheet, the proximal or bottom edge of the back sheet 57*p* extending longitudinally past the proximal or bottom edge 57 of the front sheet and forming a flap FCS, the flap FCS being readily detachably interconnected to a mount sheet 10*bs*, the mount sheet 10*bs* being fixedly attached to the mount 500, each individual glove 10 being readily detachable from the mount sheet 10*bs* via manual pulling on an outermost mounted one 10*tm* of the gloves away from the mount sheet 10*bs*.

In such an apparatus, the flap FCS is readily detachably interconnected to the mount sheet 10*bs* via a series of adjacent perforations 57*p* formed in sequential linear or curvilinear arrangement or seam 57*p* in a sheet of the polymeric material that extends between the flap FCS and the mount sheet 10*bs*.

In another aspect of the invention there is provided a method of delivering a series of gloves to a user in serial fashion comprising mounting a stack of gloves as described above on the mount 500 in an arrangement wherein an outermost glove 10*ts* in the stack is readily manually engageable by a user to pull the outermost glove 10*ts* apart from the mount sheet 10*bs*.

In another aspect of the invention, the present invention provides an apparatus and method for delivering a disposable glove from a roll of connected gloves such that the user can simply manually grab the distal open end of a distalmost glove on the roll and immediately insert a hand into the glove where the distal end of the glove on the roll is already open to enable faster insertion of the hand to best minimize contact with ambient microorganisms, chemicals or other matter.

The apparatus preferably provides a serially deliverable plurality of gloves that are attached to each other in roll form and separable from each other by pulling one glove at the end of the roll with relatively minor pulling force away from the bottom of the next glove on the roll to which the top of the glove being pulled is attached. The roll typically comprises a rolled up cylinder of flattened plastic gloves attached serially or sequentially to each other from top end (tip end of finger) to bottom end (bottom tip end of the wrist portion of the glove). The last glove on the outside of the roll is arranged such that the open end of the glove is at the distal end and the proximal tip end of one of the fingers is readily detachably attached to the open or openable proximal wrist end of the immediately sequentially next glove in the series on the roll. When the distal-most end glove on the roll is detached, the next glove from which the distal-most glove has been detached is left behind such that the open or openable wrist end of the glove is left open upon detachment.

Each glove is formed and adapted to comprise a pair of opposing thin sheets of flexible polymer material that are adjoined to each other around a perimeter or circumferential edge to form five fingers and a wrist portion of a glove having an enclosed interior formed between the opposing sheets of polymer material.

The roll of serially attached gloves is typically rolled up as a cylinder having a center axial aperture which can be mounted on a support rod such that the cylinder can be rotated around the rod and gloves serially delivered as one is detached.

The tip distal end of one glove is detachably attached along a line of perforations to the tip proximal end of the wrist portion of an immediately serially adjacent glove. Two attached gloves can readily be torn apart from each other manually by the user. The gloves are configured to have an overall upstream to downstream length that will accommodate both receipt of the length of the fingers within the receptacles and receipt and coverage of the length of the palm of the hand up to at least the point of the wrist of a larger than normal sized hand.

In one embodiment the polymeric material comprising the gloves comprises a sheet of flexible material having a thickness of typically less than about 500 microns and more typically less than about 100 microns. The sheet material itself typically comprises a woven or punch formed fabric, a paper material or a solid polymeric material comprised of one or more of polymers such as polyethylene, polypropylene, polyester or the like.

The number and frequency of successive perforations provided along the perforated seamed lines of attachment and separation seams between successively attached gloves are preferably configured to be of such a size and with such regularity that successive individual gloves can be readily detached from each other, an opening being formed when two successive bags are detached from each other along the perforated bottom end of the proximal wrist portion of the gloves.

The continuum of gloves on the roll of bags is arranged such that the distal-most end of the distal-most glove on the roll of gloves is the open end with the detached tip end of the finger remaining closed, an open end of the wrist portion being immediately accessible and available to the user to insert the user's hand when detached from the roll. The remainder of the gloves in the cylindrical roll are insulated from engagement with a user's hand or other body part due to the formation of the roll which encloses the remaining gloves from exposure to the open environment.

The present invention therefore provides a roll of enclosed gloves adapted to function as a glove, the gloves being sequentially attached to each other along a readily separable seam line, the seam line typically comprising a seam having a series of perforations along the seam line that weaken the seam line such that two attached gloves can be separated from each other by relatively minor manual pulling force. The gloves are preferably attached sequentially to each other and formed into a compact cylindrical roll of gloves comprised of parallel arranged flattened sheets of flexible polymeric material. Each individual glove preferably comprises two opposing sheets attached along two opposing continuous edges of polymer material and attached at top and bottom edges to successive bottom and top edges of successive gloves, the top and bottom edge attachments being readily separable.

A glove apparatus according to the invention therefore can comprise a series of interconnected gloves, each glove having a wrist end 55 having a proximal terminal edge 59 and a finger end having a distal terminal edge 67, the terminal edge 59 of one glove being readily detachably attached to the proximal terminal edge 59 of an immediately adjacent glove, each glove comprising a thumb receiving portion 105 and a multiple finger receiving portion 120, the distal terminal edge 67 that is readily detachably attached being disposed along a distal terminal edge of the multiple finger receiving portion 120, 108, the glove 10 comprising a pair of opposing flexible thin walled sheets 50, 60 of plastic, polymer or fabric joined to each other along a perimeter to form an enclosed space between the sheets forming a glove 10 readily detachable from another glove, the proximal terminal edge 59 of the detached glove 10*d* forming an open terminal wrist end 59*o* upon detachment such that a human hand can be inserted through the open wrist edge 59*o* and into an enclosure formed between the pair of sheets that are joined around their perimeter.

A roll of such gloves can be easily mounted in a readily manually accessible location in every room or hallway of a medical institution.

In one embodiment of the invention individual gloves in a roll of successively attached glove can comprise three receptacles comprised of at least a first receptacle configured and having a complementary receiving aperture adapted to receive a thumb of human hand, a second receptacle configured and having a complementary receiving aperture adapted to receive at least the index or forefinger of a human user and third receptacle configured and having a complementary receiving aperture adapted to receive at least two or more of the other fingers of human hand. In such an embodiment, the distal top edge of the third receptacle is attached to the bottom or proximal edge of an immediately preceding glove in the roll of successively attached gloves, the two successively attached gloves being readily detachable from each other along a line of attachment between the edges.

In another embodiment of the invention individual gloves in a roll of successively attached glove can comprise five receptacles comprised of a first receptacle configured and having a complementary receiving aperture adapted to receive a thumb of human hand, a second receptacle configured and having a complementary receiving aperture adapted to receive at least the index or forefinger of a human user, a third receptacle configured and having a complementary receiving aperture adapted to receive the middle finger of a human hand, a fourth receptacle configured and having a complementary receiving aperture adapted to receive the ring finger of a human hand and a fifth receptacle configured and having a complementary receiving aperture adapted to receive the little finger of a human hand. In such an embodiment, the distal top edge of at least two of the second, third, fourth and fifth receptacles is attached to the bottom or proximal edge of an immediately preceding glove in the roll of successively attached gloves, the two successively attached gloves being readily detachable from each other along a line of attachment between the attached edges.

In another embodiment of the invention there is provided a series of gloves mounted in a stack on a mount, each individual glove in the stack comprising a top or front thin sheet and a bottom or back thin sheet, the top and bottom sheets formed integrally together to form a flexible glove having at least five receptacles comprised of a first receptacle configured and having a complementary receiving aperture adapted to receive a thumb of human hand, a second receptacle configured and having a complementary receiving aperture adapted to receive at least the index or forefinger of a human user, a third receptacle configured and having a complementary receiving aperture adapted to receive the middle finger of a human hand, a fourth receptacle configured and having a complementary receiving aperture adapted to receive the ring finger of a human hand and a fifth receptacle configured and having a complementary receiving aperture adapted to receive the little finger of a human hand. The front and back sheets each have a different front and back longitudinal length respectively extending from a common distal or top edge of the longest finger receptacle to a different proximal or bottom edge of each of the front (or top) and back (or bottom) sides or sheets of the glove respectively. The longitudinal length of the back (or top) sheet is longer than the longitudinal length of the front (or bottom) sheet, the proximal or bottom edge of the back (or top) sheet extending longitudinally past the proximal or bottom edge of the back or top sheet and forming a flap, the flap having a line of perforations extending laterally across the flap forming a proximal-most strip attached along the line of perforations to the proximal edge of the back or top, the perforations being adapted to enable a user to readily detach the back or top sheet from the proximal-most strip. The proximal-most strip of the back or top sheet is adapted to be readily mountable on a mount such that each individual glove is arranged in a stack of flat gloves one on top of each other.

DETAILED DESCRIPTION OF INVENTION

Figure 1:
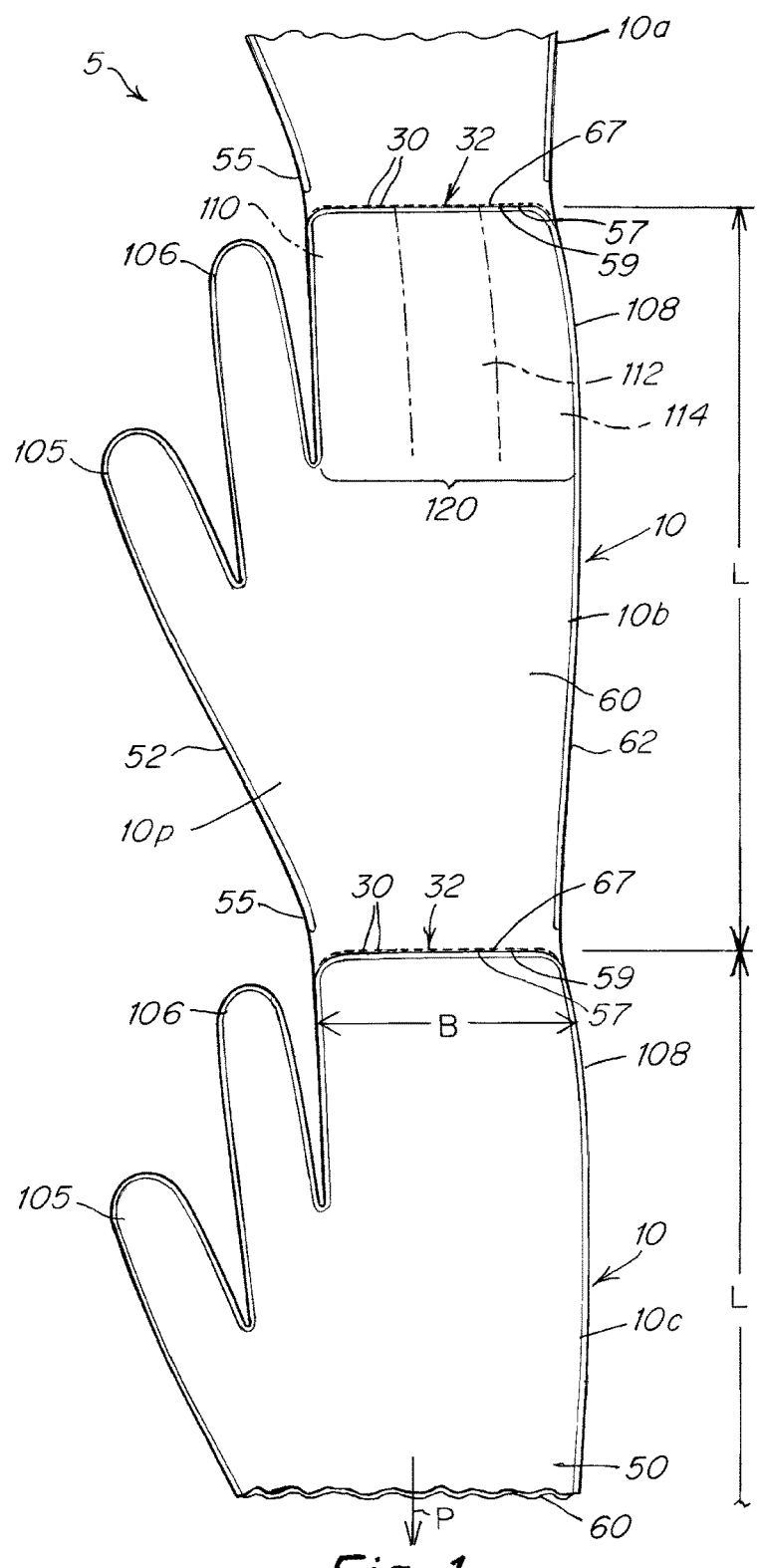
FIG. 1 is a top plan view of a length of a roll of successively attached gloves that are readily detachable from each other in accordance with the invention.
Figure 2:
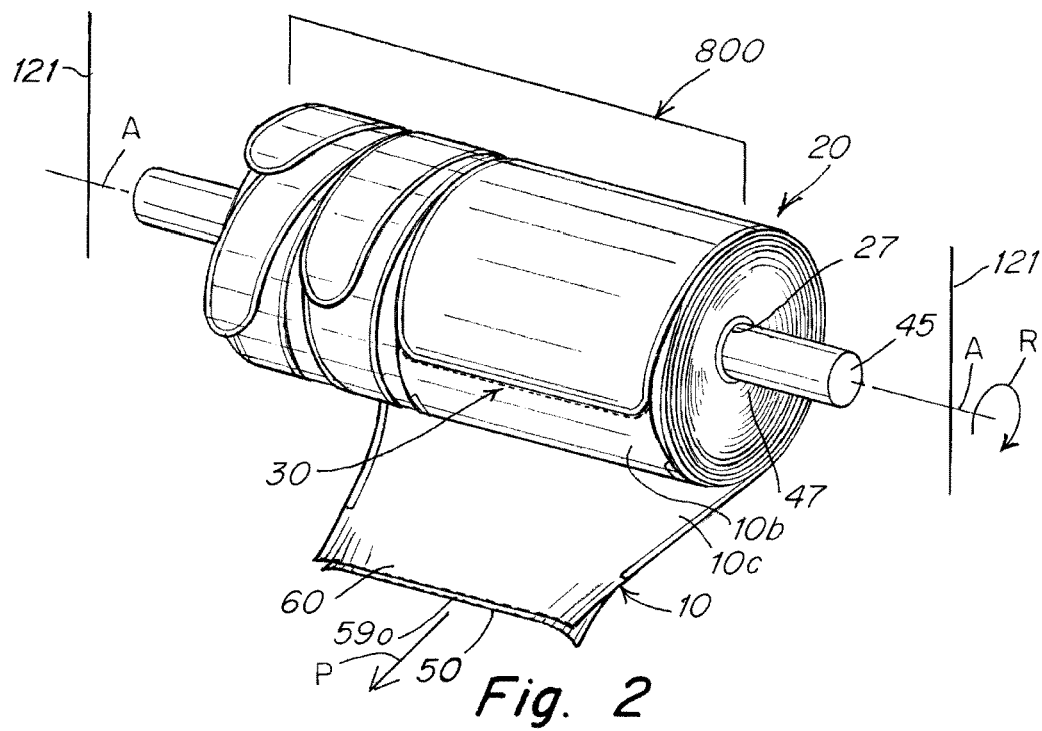
FIG. 2 is a side perspective view of a roll of multiple serially attached gloves according to the invention rolled up into a cylinder form.
Figure 3:
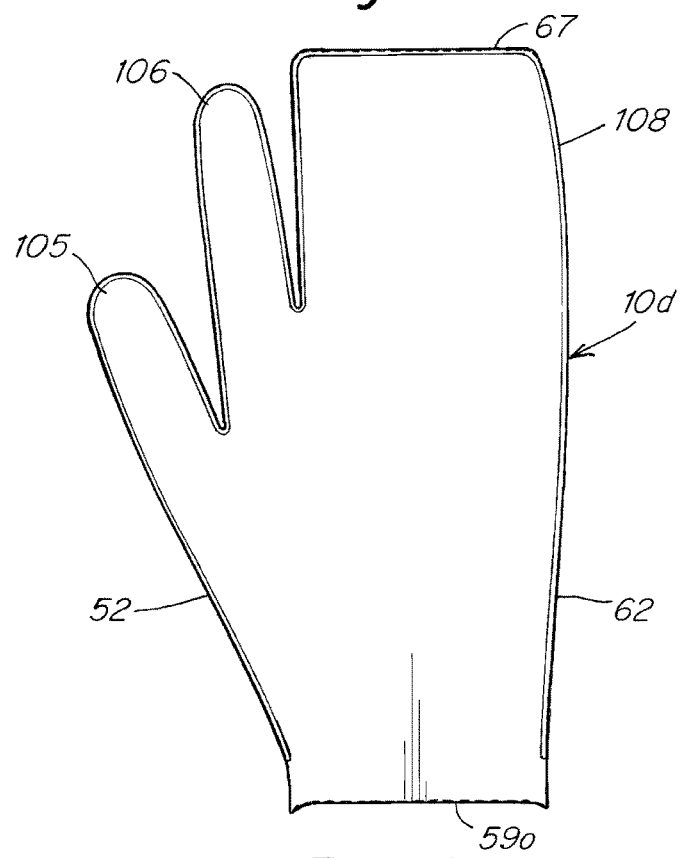
FIG. 3 is a top plan view of a detached glove as shown in FIG. 1 according to the invention.
Figure 4:
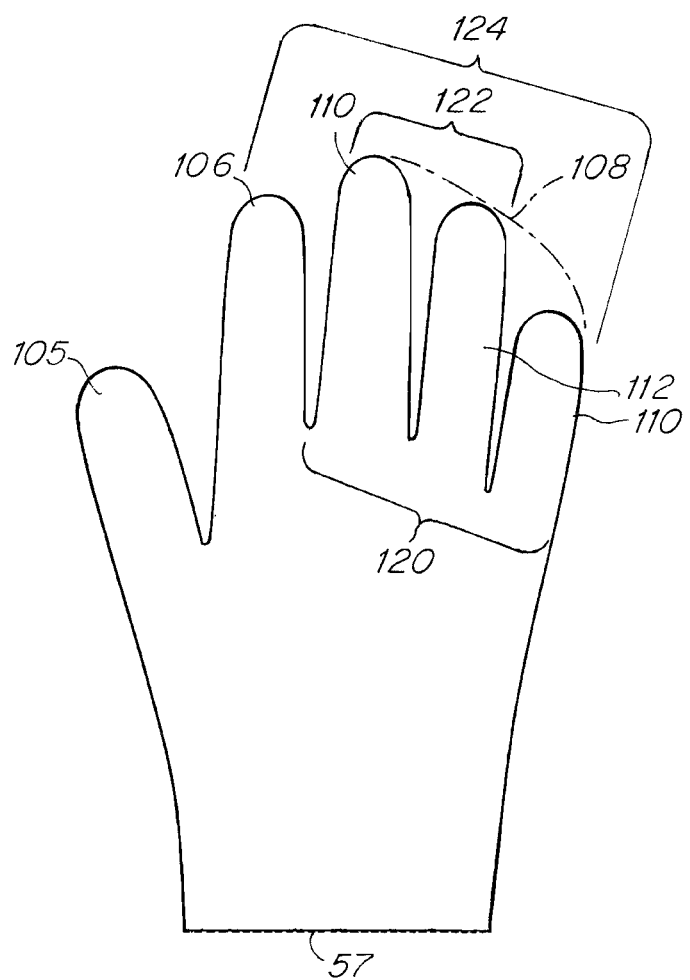
FIG. 4 is a top view of a five separate fingered glove showing in schematic how a multiplicity of fingers are combined into a single multiple finger receiving member 120, 108 to form a glove as shown in FIGS. 1, 2, 3 according to the invention.

FIG. 1 shows consecutively interconnected gloves 10 that can be rolled up into a roll 20, FIG. 2, each glove 10 comprising a first upper sheet 60 that is connected along opposing side edges 52, 62 to an opposing bottom sheet 50. Consecutive gloves 10 are interconnected to each other along a relatively thin line 32 of polymeric material that has a series of perforations 30 extending along the tip distal edge 67 of a selected multiple finger receiving portion 108 of the glove 10 that extends the width B of the multiple finger receiving portion 108 and is detachably attached to the proximal tip bottom edge 57 of the wrist portion 55 of an immediately adjacent glove 10.

The line 32 has a sufficient number of perforations 30 such that an individual glove 10 can be readily detached along the line 32 of perforations 30 from an adjacent glove 10 by steadily pulling one proximal bag away from the serially attached glove by hand under light manual force.

As shown in FIG. 1 the multiple finger receiving portion 108 of the glove 10 is formed and adapted to accommodate interior receiving space that effectively combines multiple fingers 110 (middle), 112 (ring), 114 (pinky) into a single three finger receiving space in the nature of a mitten. In the FIG. 1 embodiment, the multiple finger receiving portion 108, 120 accommodates three (3) human fingers but could comprise and accommodate two fingers 122 or four fingers 124.

In the FIG. 1 embodiment, the glove comprises a thumb receiving portion 105, an index finger receiving portion 106 and a combined three finger 108 receiving portion 120.

As shown in FIG. 2, a series of multiple or plurality of gloves 10 serially attached to each other as in FIG. 1 can be rolled up into a cylinder form 20 leaving an open central axial aperture 27 in the cylinder that can be readily rotatably mounted on a support rod 45 that can be readily mounted on a wall or within an enclosed box (not shown). The rolled up cylinder 20 is formed such that the gloves on the interior body portion 47 of the cylinder are enclosed, covered and protected from exposure to the surrounding air and environment generally thus serving to maintain the gloves in a relatively sterile environment while rolled up on the roll 20.

Figure 5:
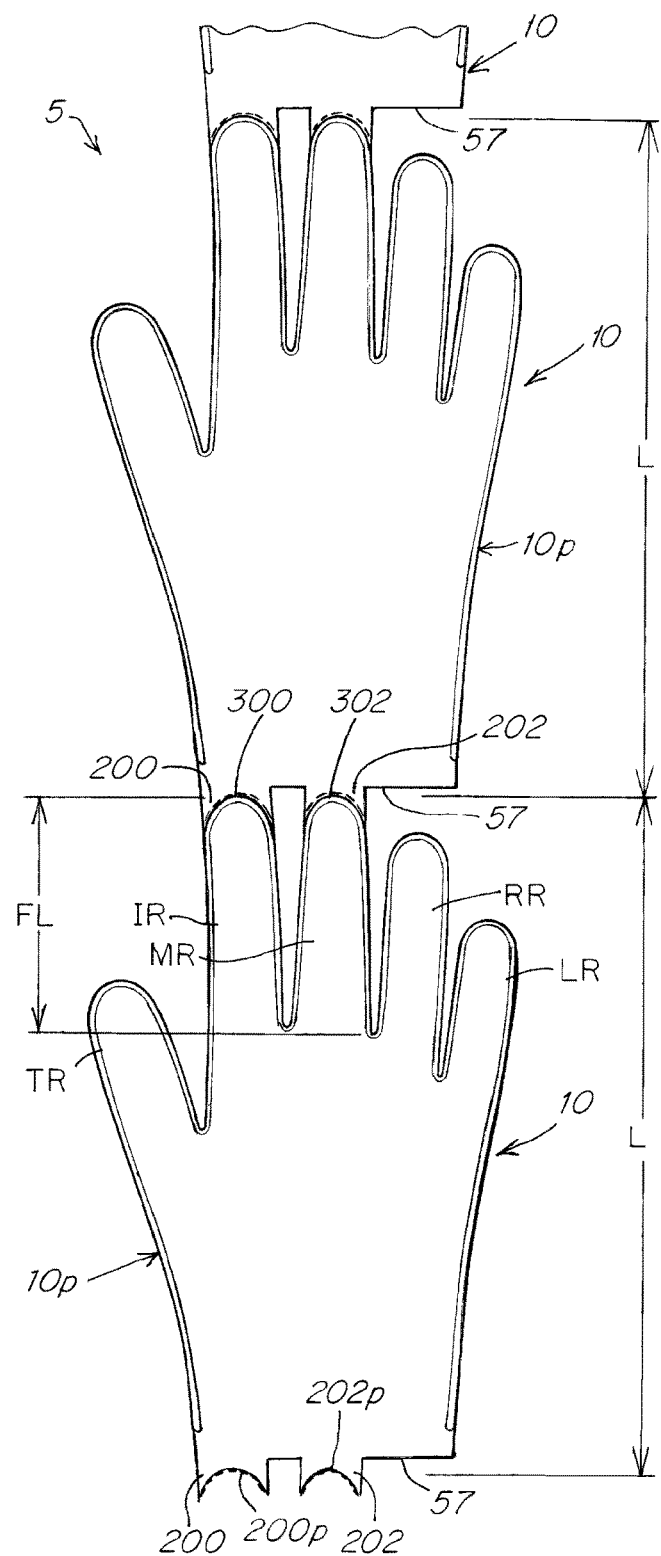
FIG. 5 is a top plan view of another embodiment of the invention showing a section of a roll of successively attached gloves having five separate fingers that are readily detachable from each other at the distal tip ends of two of the five fingers, the forefinger and the middle finger.
Figure 6:
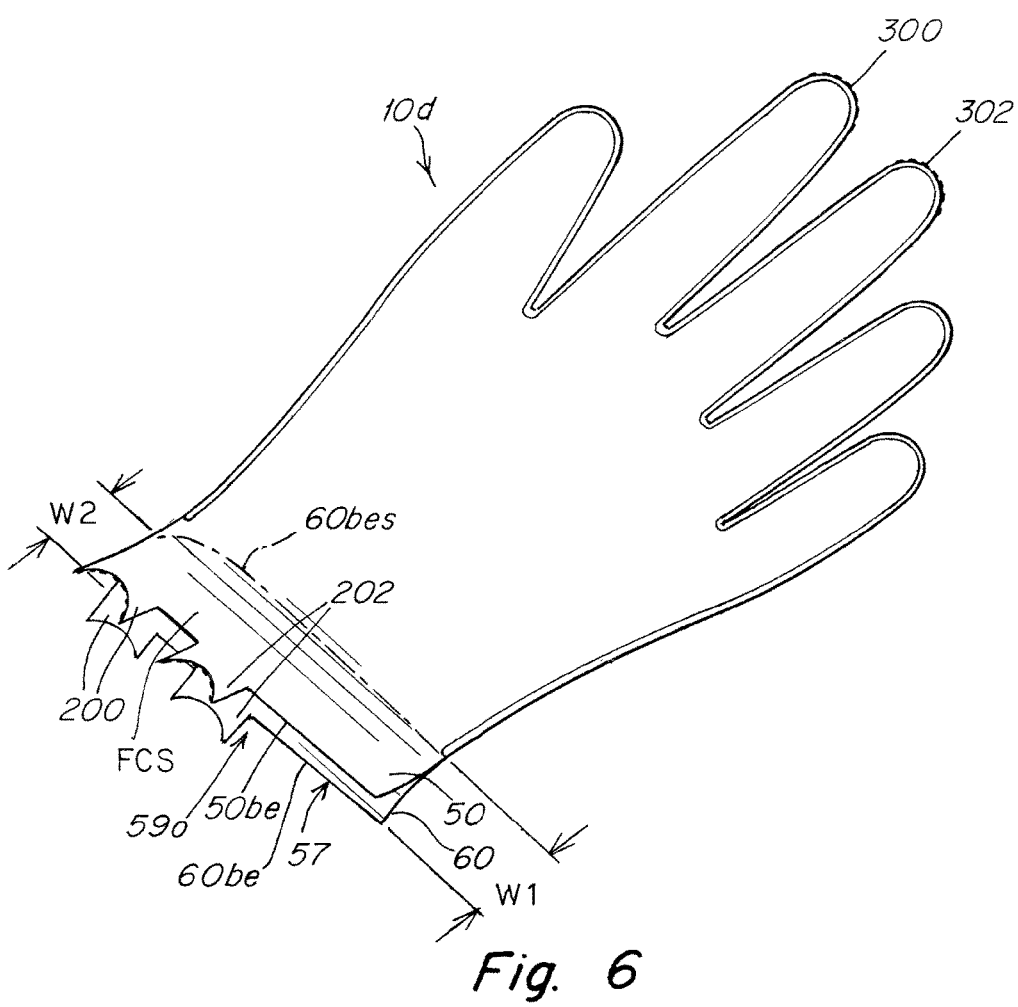
FIG. 6 is a top plan view similar to FIG. 5 showing the details of the bottom edge of a glove in the roll after an immediately successive glove has been detached therefrom.

FIGS. 5, 6, 7, 8 show an alternative embodiment of the invention where the glove 10 has five separate fingers or finger receptacles a thumb receptacle TR, an index finger receptacle IR, a middle finger receptacle MR, a ring finger receptacle RR and a little finger receptacle LR. In the embodiment shown in FIGS. 5, 6, the distal-most edges 300, 302 of at least two of the five finger receptacles, IR, MR of an individual glove 10 are readily detachably attached to the bottom-most edge 57 of an immediately preceding glove 10 in a roll series of serially attached gloves 10. As shown in FIGS. 5, 6 the distal-most edges 300, 302 are typically detachably attached to attachment extensions 200, 202 that extend from the proximal or bottom-most edge 57 of a glove via a series of perforations 200p, 202p formed in and between the junction of the plastic sheet material that is disposed between the lower edges of extensions 200, 202 and the top edges 300, 302 of finger receptacles IR, MR.

Figure 7:
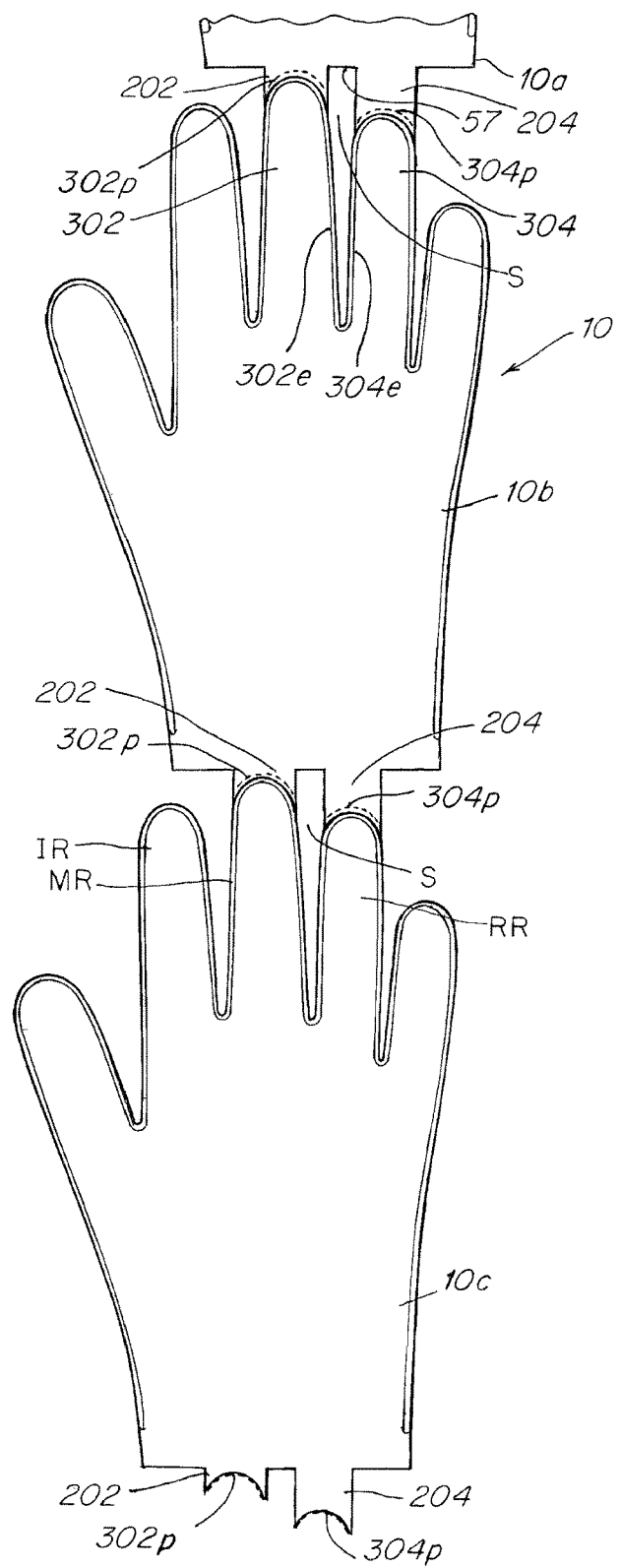
FIG. 7 is a top plan view, similar to FIG. 5, of another embodiment of the invention showing a section of a roll of successively attached gloves having five separate fingers that are readily detachable from each other at the distal tip ends of two other of the five fingers different from the FIG. 5 embodiment, the middle finger and the ring finger.
Figure 8:
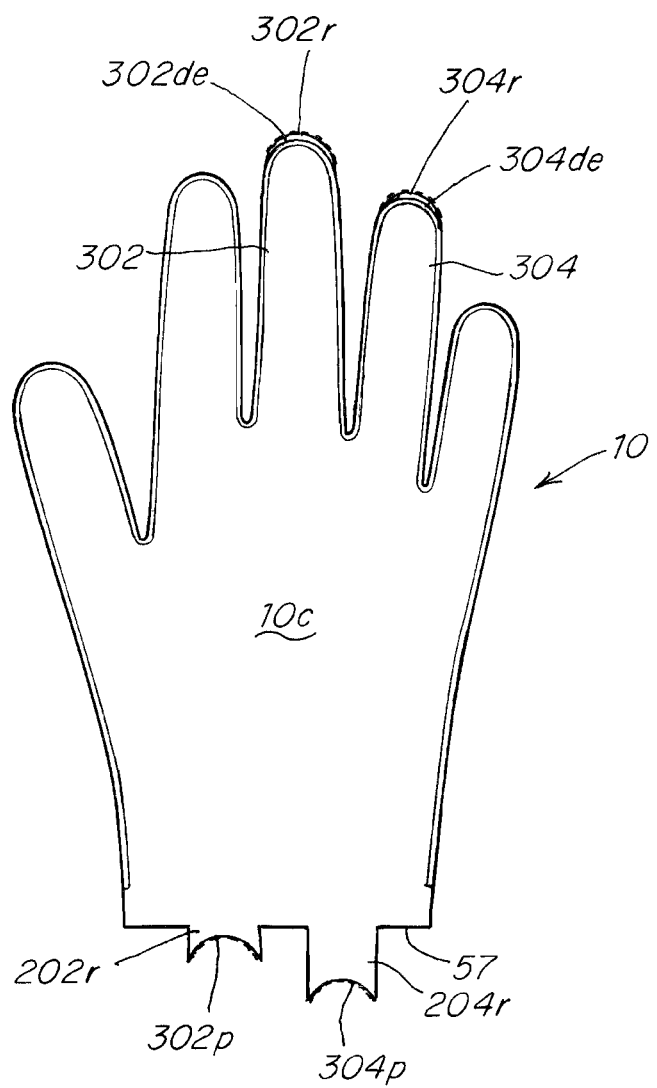
FIG. 8 is a top plan view similar to FIG. 7 showing a glove in the roll of FIG. 7 after an immediately successive glove has been detached therefrom.

In an alternative embodiment shown in FIGS. 7, 8, the readily detachable perforations 302p, 304p are disposed between the top edges of the middle finger MR and the ring finger RR and the bottom edges of extensions 202, 204.

As can be readily imagined the bottom edge 57, 60 of a five fingered glove as shown in FIGS. 5, 6, 7, 8, can be provided with attachment extensions that correspond to the top edges of any selected one finger or a multipliclity of two, three, four or five fingers such that any one or two or three or four or all five fingers can be detachably interconnected to the bottom edge 57, 60 of an upstream glove 10. Preferably the top edges of at least two fingers are detachably attached to each other, most preferably two fingers.

As with the FIGS. 1, 2, 3, 4 embodiment, each individual glove 10 of the FIGS. 5, 6, 7, 8, 9 embodiment comprises a generally planar or flat top sheet 50 that overlies in a generally parallel disposition a bottom generally planar or flat bottom sheet 60.

In the embodiment shown in FIGS. 5, 6, 7, 8, 9, the bottommost edges 50be, 60be extend longitudinally about the same distance from the tip end surfaces 300, 302 of the fingers. And both of the bottom edges 50be and 60be have connector extensions 200, 202, FIG. 6. In an alternative embodiment, one or the other of the lengths of the top 50 or bottom 60 sheets can be longer than the other by a length W1 or W2 such that the bottommost edge 50be or 60be extends beyond the other of the two edges. By way of example with reference to FIG. 6, the bottom sheet 60 could be configured to have a bottommost edge 60bes that is spaced upstream of the bottommost edge 50be such that a flap FCS is formed at the bottom edge 57 of the glove 10 enabling the user to more easily manually engage and separate the two sheets 50, 60 from each other to create an opening at the end 57 by which a user can readily insert their hand into the enclosed interior space IS that is disposed between the top 50 and bottom 60 sheets. In such an embodiment, the sheet 50 or 60 that is shorter in length would typically not include attachment or connector extensions 200, 202, the only connection between the finger edges 300, 302 and the bottom edge 57 of a glove being between connector extensions that extend from one and not both of the two sheets 50, 60.

Figure 9:
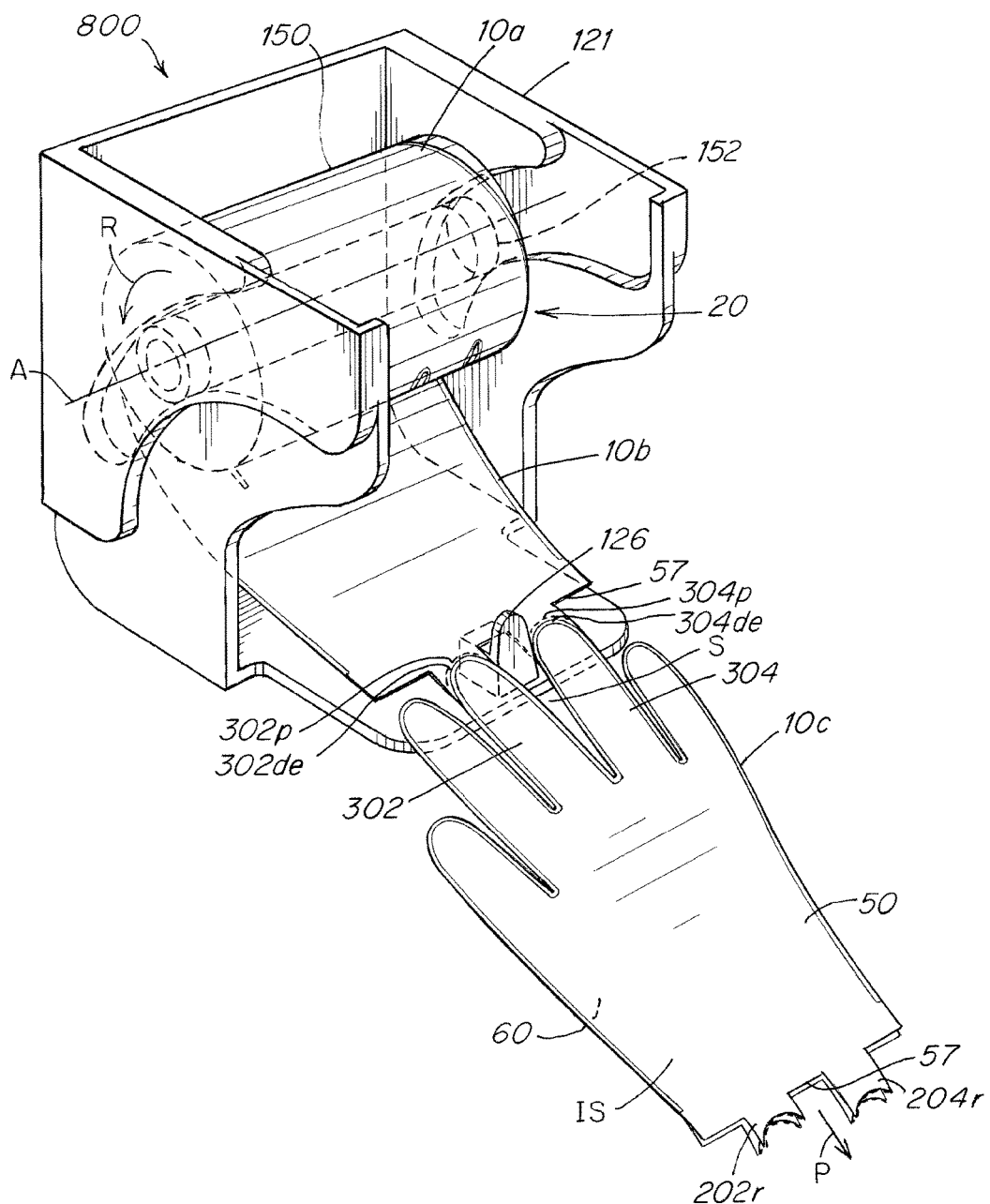
FIG. 9 is a top left perspective view of a dispenser for a roll of gloves of the FIGS. 7, 8 embodiment according to the invention showing the last glove undetached glove at the end of the roll mounted in a position relative to the roll of gloves such that the last glove can be manually pulled by a user and the space between adjacent attachment extensions on the ends of the middle and ring fingers can be readily aligned with a detent that upon pulling of the last glove backwardly results in the bottom edge of the immediately upstream glove engaging the detent enabling ready tearing of the perforations along the distal ends of the middle and ring fingers of the last glove so that the last glove is readily detached from the immediately upstream glove attached to the last glove.
Figure 10:
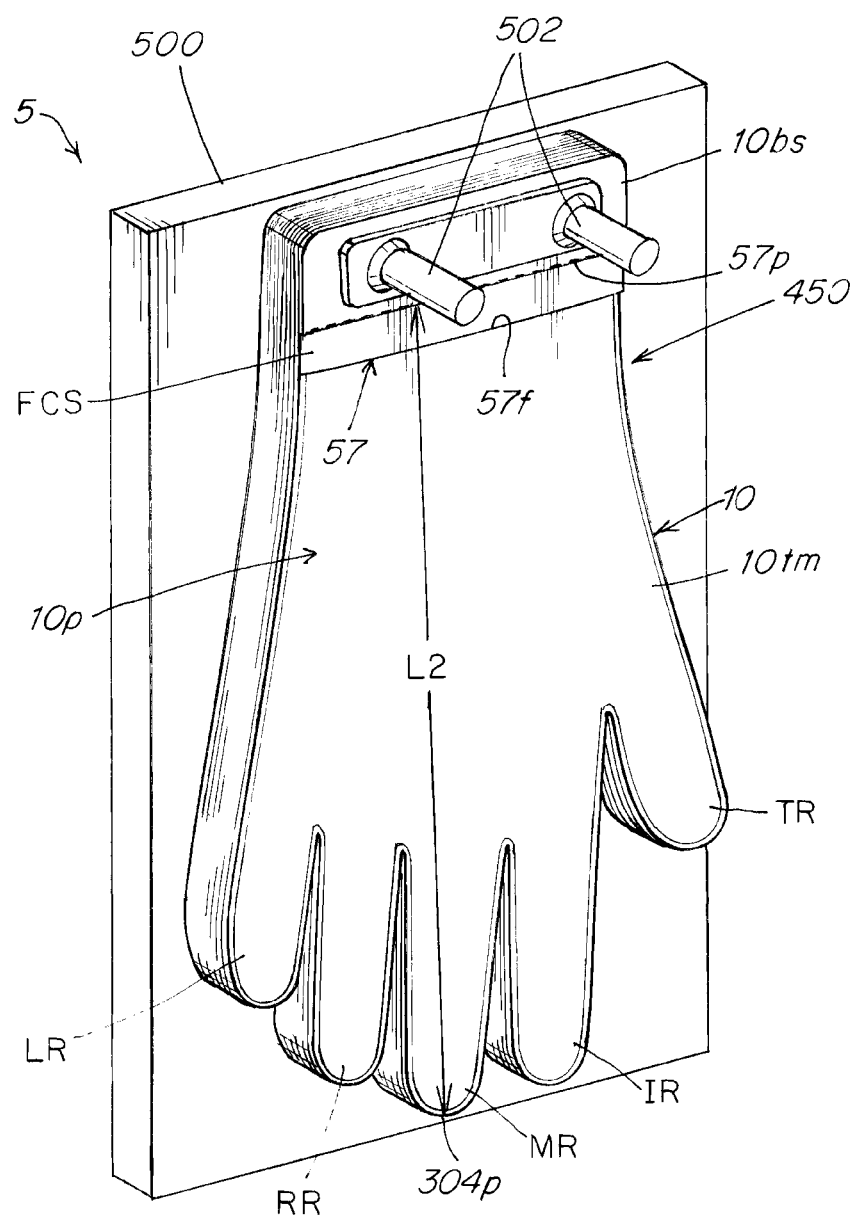
FIG. 10 is a side perspective view of a stack of gloves according to another embodiment of the invention where each glove in the stack has a perforated bottom edge that is readily detachably attached to a manifold that is attached to a support stand.

As shown in FIG. 9, a dispenser 800 can be provided having a housing 121 on which a cylindrical tube or mount 152 can be mounted for rotation R around the axis A of the cylinder. A plurality of successively attached gloves such as 10a, 10b, 10c can be formed into a cylindrical roll that can be rolled up onto the outer circumference of the cylindrical tube or mount 152. The last glove in the roll 10c can be manually pulled with force P so as to unwind the roll of gloves from the rotatable R cylindrical mount or tube 152. The detachment or interference finger or detent 126 is arranged and mounted on the housing 152 in an arrangement wherein the user can readily manually align the slot S formed between the detachably attached fingers of last glove 10c and the corresponding extensions 202, 204 on the bottom edge of the immediately upstream glove 10b with the finger or detent 126. As shown in FIG. 10, the user can readily manually grasp the last glove 10c on the roll 150 of gloves and pull P with the detachment finger or detent 126 disposed within the slot S such that on continued downstream pulling P, the downstream edge of glove 10b is prevented from travelling in the direction of the force P and the perforations 302p, 304p on the distal-most circumferential edges 302de, 304de are subject to tearing away from the attachment extensions 202, 204 whereby the downstream glove 10c detaches from upstream glove 10b on continued exertion of pulling force P by the user such that a completely detached glove 10c, FIG. 8 results from the user's exertion of pulling force P. The resulting detached glove 10c has small leftover residues 202res, 204res attached to the bottom edge 57 of the glove 10c and a very small residue 302r and 304r remaining attached to the distal-most outer circumferential edges of the fingers 302, 304.

In the embodiment shown in FIGS. 5, 6, 7, 8, 9, the three (3) end-most gloves 10a, 10b, 10c of the roll 150 of successively interconnected gloves are shown. FIG. 8 shows the last glove 10c on the roll 150 after the glove 10c has been detached from its immediately upstream attached glove 10b. As shown the distal-most circumferential end surfaces 302de, 304de of the adjacent fingers 302, 304 are curved in their contour. As shown the preferred fingers for attachment to the downstream edge 57 of an adjacent glove are any two adjacent ones of the middle three fingers IR, MR (or 302) and RR (or 304).

As shown in FIGS. 6, 7, 8, 9 any two successively attached gloves such as 10a/10b or 10b/10c, are provided and configured with attachment extensions 202 and 204 that extend between the bottom edge 57 of one glove 10a, 10b, 10c and the distal-most circumferential edges 302de and 304de of an immediately downstream attached glove 10b or 10c. In this embodiment, the perforations 302p, 304p that are disposed within the attachment extensions 202 and 204 are arranged to extend in a complementary curved pattern to and along the curved distal-most circumferential edge surfaces 302de and 304de of the two adjacent fingers 302, 304 (or IR and MR) that are provided with the attachment extensions.

The perforations 57p are disposed as close as possible to and the distal-most circumferential surfaces 302de, 304de so that when the perforations 302p, 304p of last glove 10c are torn apart and the last glove 10c is subsequently detached from an immediately upstream formerly attached glove 10b, the portion 302r, 304r, FIGS. 7, 8, 9 of the attachment extension 202, 204 that remains attached to the end surfaces 302de, 304de of the detached glove 10c is so minimal in size as not to interfere with a user's ability to manually manipulate and use the fingers 302, 304 to grab or engage other objects.

As shown in FIGS. 7, 8, 9 the distal-most edges 302de, 304de of the at least two adjacent fingers 302, 304 are configured and arranged in their attachment between downstream edge 57 and edges 302de and 304de such that an enclosed slot or intermediate space S is formed between the bottom edge 57 and the side edges of the two adjacent fingers 302, 304. The enclosed space S that is so formed thus provides a conveniently located slot S into which an interference or detachment finger or detent 126 can be inserted by a user for purposes of detaching the last glove 10c from the immediately upstream glove 10b where a roll 150 of such successively interconnected gloves is formed.

Figure 11:
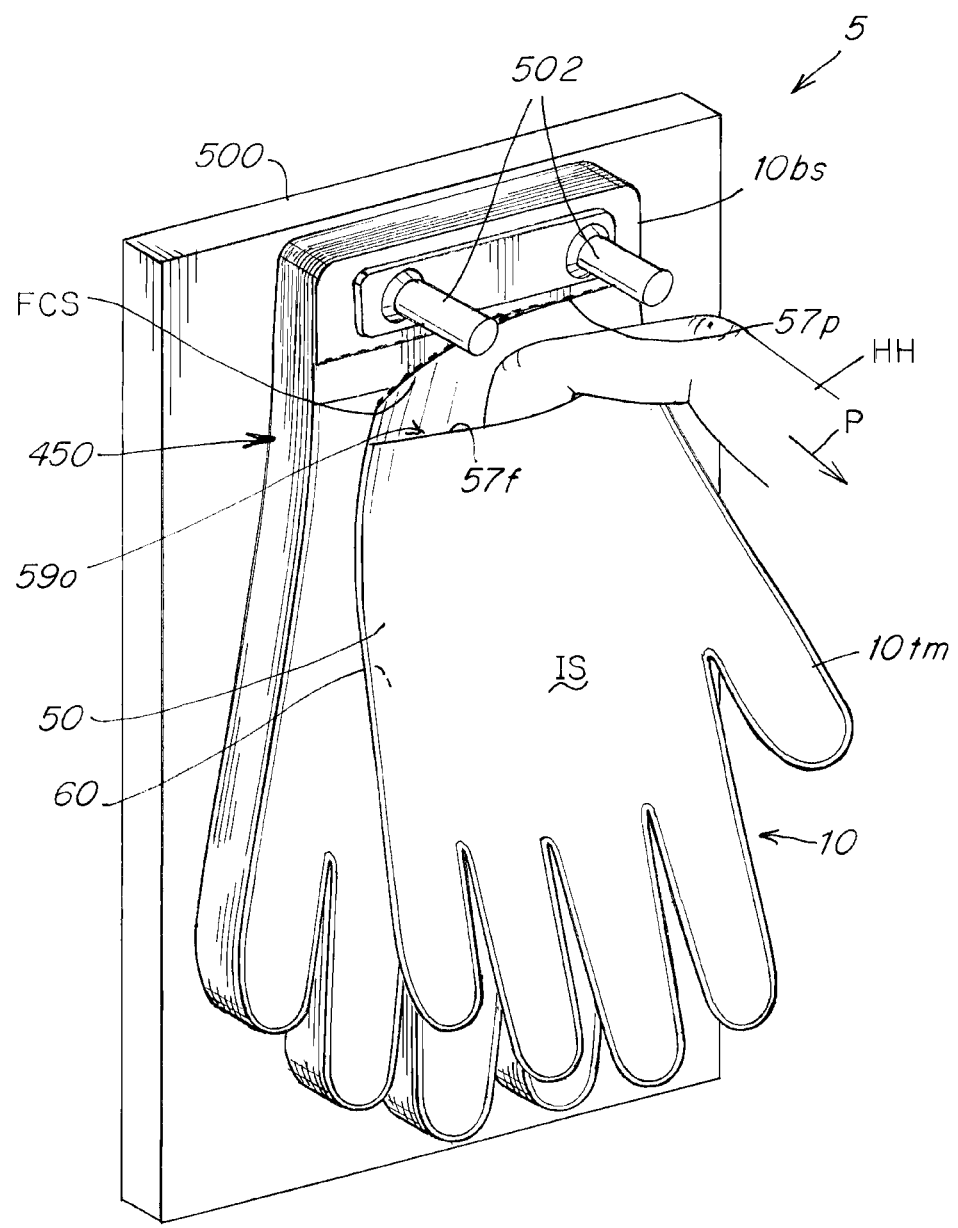
FIG. 11 is view similar to FIG. 10 showing a user pulling downwardly on the glove that is on the top of the stack of gloves so as to cause the top glove to detach from the manifold along the perforated edge of the glove attached to the manifold.
Figure 12:
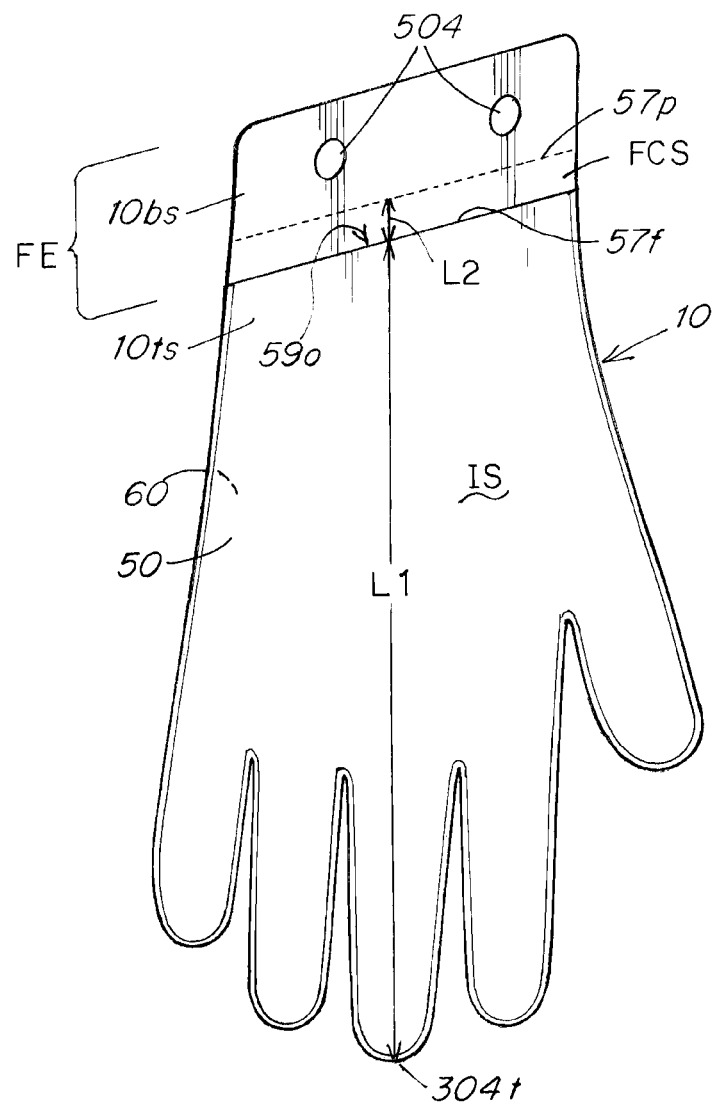
FIG. 12 is a side perspective view of a single glove separated from the stack of gloves shown in FIG. 10 showing the relationship and structure of the manifold, the perforations and the bottom edge of the glove.

In the FIGS. 6, 7, 8, 9 embodiment, one or the other of the top or bottom sheets FIGS. 10, 11, 12 show in a top side perspective view, of another embodiment of the invention that is configured as a stack 450 of individual gloves 10 that is mountable via a mounting strip 10bs that extends proximally from the perforated seam 57p that extends along the bottom edge of the bottom sheet 60 of a glove 10, the strip 10bs being mountable to the mount base 500 via mounting apertures 504 that are received by and mounted on one or more complementary support rods 502 extending from a mounting base 500 such that the stack 450 of gloves 10 is arranged and mounted in a stack arrangement on the mounting base 500. The top-most glove 10tm in the stack 450 is thus readily manually accessible by a user to manually engage, grab and tear the topmost glove 10tm off from the mounting rods 502 while the glove 10tm is mounted on the rods 502 along a line of perforations 57p extending laterally along the width of the flap FCS.

As shown in FIGS. 10, 11, 12 a flap extension FE extends longitudinally from the bottom edge 57 of a glove, comprises a flap portion FCS of the bottom sheet and a mounting strip portion 10bs that are attached to each other along the line of perforations 57p that enables user to tear a glove 10 in a stack 450 from the rods 502 when a glove is mounted via the mounting apertures 504.

Figure 13:
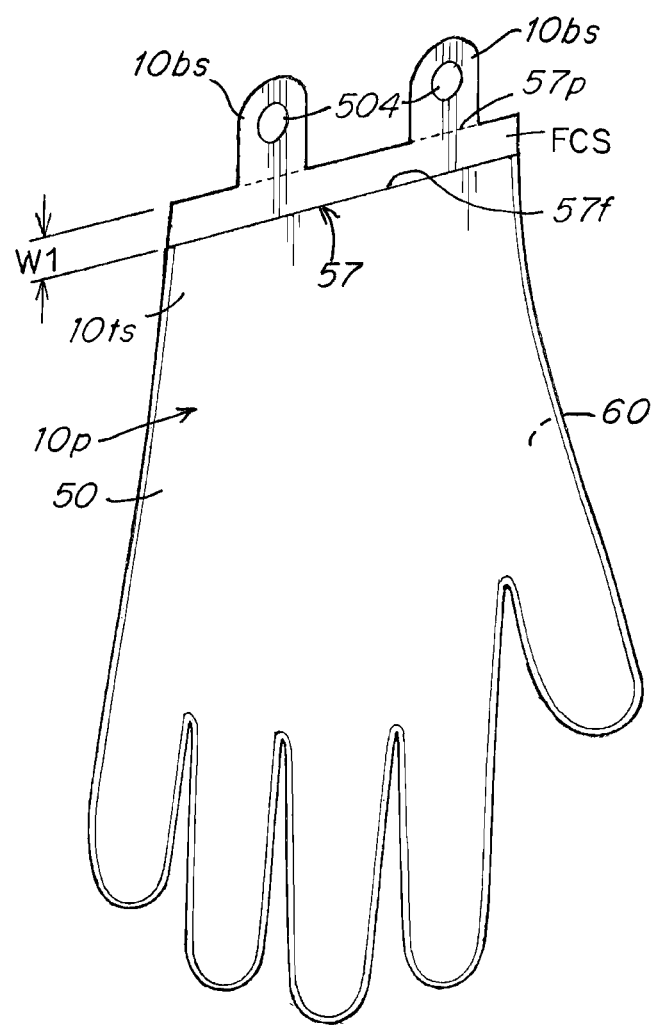
FIG. 13 is a side perspective view of another embodiment of a glove configuration that can be mounted in a stack on a support stand, showing a glove a single glove separated from the stack where, instead of a full lengthwise manifold that extends the full width or length of the bottom edge of the glove, is provided with individual manifold extensions detachably connected to the bottom edge of a glove via perforations.

In an alternative embodiment shown in FIG. 13, the apparatus includes individual mounting strips or tabs 10bs having each receiving apertures 504 that are attached to the distal-most edge of the flap portion FCS that extends from the bottom edge 57 of the bottom sheet 60 of the glove 10.

In the FIGS. 10, 11, 12, 13 embodiments, once a glove 10 is detached along the perforated line 57p, the resulting standalone glove 10 has a flap FCS extending W1 from the edge of the bottom 60 sheet of the glove providing as described above a better manually manipulable ability to the user to separate the two sheets 50, 60 at the bottom edge to enable ready insertion of the user's hand into the enclosed interior space IS of the glove 10.

In all of the embodiments described herein the top 50 and bottom 60 sheets are generally flexible planar sheets arranged and attached to each other in generally parallel disposition. The top 50 and bottom 60 sheets are sealably attached to each other around their the entirety of their circumferential peripheries except at the bottom edge 57 such that an enclosed interior space IS is formed between the top 50 and bottom sheets with the bottom edges 57 of the two sheets 50, 60 remaining not attached so that a user can manually separate the bottom edges 57 of the two sheets 50, 60 with the aid of the flap FCS of sheet 60 extending W1 longitudinally L2 beyond the longitudinal L1 length of the top sheet 50. The flap FCS thus better enables the user to manually access the lip 57f of the edge 57 of the top sheet 50 and to open the end 59o as well as to provide a vehicle for mounting the glove 10 to the mounting strip 10bs via seam 57p.

As shown in FIG. 11, the unsealed opening 59o provides both a vehicle for a user to readily manually grab an edge 57f of the opening 59o which enables the user to readily manually pull P the outermost glove 10tm away from the stack 450 as well as to tear the seam 57p and separate the glove 10tm completely from the mounting strip 10bs. The unsealed opening is also configured to provide a large enough aperture or opening for a human hand HH to be inserted completely within the enclosed interior space IS.

What is claimed is:

1. An apparatus enabling serial delivery of a plurality of interconnected gloves, the apparatus comprising:

a plurality of flexible gloves, each flexible glove comprised of a top and a bottom sheet of polymeric material each having a length, the top and bottom sheets being sealably attached to each other in an arrangement that forms five enclosed fingers adapted to generally receive five fingers of a human hand, and an enclosed palm portion having an open bottom end adapted to generally receive a palm of a human hand, a distal tip end of one or more of the fingers of a downstream one the plurality of gloves being readily detachably attached to a bottom proximal edge of the open bottom end of an immediately upstream one of the plurality gloves, the attached upstream and downstream gloves forming a continuum of serially attached gloves formed into a cylinder or roll, each of the serially attached gloves having a longitude generally extending from the distal tip end of the one or more fingers to the open bottom end, the serially attached downstream and upstream ones of the plurality of gloves being readily detachable from each other by exertion of human manual pulling force on one or both of the serially attached gloves wherein the pulling force is exerted in a direction along the longitude of the serially attached gloves that pulls the serially attached gloves in opposite directions away from each other, a dispenser comprising a base and a complementary cylinder mounted on the base, the complementary cylinder having an axis around which the cylinder or roll of gloves is mounted and rotatable, the dispenser being adapted to enable a downstreammost glove on the roll to be manually graspable by a user to detach the fingers of the downstreammost glove from the open bottom end of an immediately upstream glove to the downstreammost glove, the length of one of the top or bottom sheet being longer than the length of the other of the top or bottom sheet such that a bottommost edge of one of the top or bottom sheet extends beyond a bottommost edge of the other of the top or bottom sheet such that a flap is formed enabling a user to manually separate the top and bottom sheets from each other.

2. The apparatus of claim 1 wherein the tip ends of at least two of the fingers of the downstream one of the serially attached gloves is readily detachably attached to the bottom proximal edge of the open bottom end of an immediately upstream one of the plurality gloves.

3. The apparatus of claim 1 wherein the downstream and upstream gloves are readily detachably attached to each other via a series of adjacent perforations formed in sequential linear or curvilinear arrangement or seam in a sheet of the polymeric material that extends between the distal tip ends of the one or more fingers of the downstream glove and the bottom proximal edge of the open bottom end of the upstream glove, the perforations being formed of a size selected to enable ready detachment along the linear or curvilinear arrangement of perforations by exertion of normal pulling force by human hand.

4. The apparatus of claim 1 wherein the sheet of polymeric material comprises a woven or punch formed fabric, a paper material or a solid polymeric material comprised of one or more of polyethylene, polypropylene, polyester or the like and wherein the sheet has a thickness of less than about 500 microns.

5. A method of delivering a series of gloves to a user in serial fashion comprising rotatably mounting a roll of interconnected gloves as claimed in claim 1 on a cylinder in an arrangement wherein a downstreammost glove on the roll is readily manually engageable by a user to pull the downstreammost glove apart from an immediately upstream attached glove.

6. The apparatus of claim 2 wherein each of the gloves has five fingers arranged and configured generally corresponding to the arrangement of a thumb, a forefinger, a middle finger, a ring finger and a pinky finger of a human hand,
wherein the tip end of either the forefinger and the middle finger or the middle finger and the ring finger are the only fingers that are readily detachably attached to the bottom proximal edge of the open bottom end of an immediately upstream one of the plurality gloves.

7. The apparatus of claim 2 wherein the at least two of the fingers of the downstream one of the serially attached gloves is readily detachably attached to the bottom proximal edge of the open bottom end of the immediately upstream one of the plurality gloves in an arrangement that forms an enclosed groove or slot between opposing edges of the at least two fingers of the immediately downstream one of the gloves and the bottom proximal edge of the open bottom end of the immediately upstream one of the gloves.

8. The apparatus of claim 7 wherein the complementary cylinder has an axis around which the roll of gloves is mounted and is rotatable, the dispenser including a detent mounted to the base in an arrangement relative to the cylinder wherein a downstreammost glove on the roll is manually graspable by a user to dispose the detent within the slot with a downstream pulling motion to forcibly engage the detent against the bottom proximal edge of a glove that is attached immediately upstream to the downstreammost glove.

9. An apparatus enabling serial delivery of a plurality of interconnected gloves, the apparatus comprising:
a plurality of flexible gloves, each flexible glove comprised of a top and a bottom sheet of polymeric material, the top and bottom sheets being sealably attached to each other in an arrangement that forms a first thumb receptacle and at least a second finger receptacle that is adapted to receive at least two other fingers of a human hand, and an enclosed palm portion having an open bottom end adapted to generally receive a palm of a human hand,
a distal tip end of the second finger receptacle being readily detachably attached to a bottom proximal edge of an open bottom end of an immediately upstream one of the plurality gloves,
the attached upstream and downstream gloves forming a continuum of serially attached gloves formed into a cylinder or roll,
each of the serially attached gloves having a longitude generally extending from the distal tip end of the second finger receptacle to the open bottom end,
the serially attached downstream and upstream ones of the plurality of gloves being readily detachable from each other by exertion of human manual pulling force on one or both of the serially attached gloves wherein the pulling force is exerted in a direction along the longitude of the serially attached gloves that pulls the serially attached gloves in opposite directions or away from each other,
a dispenser comprising a base and a complementary cylinder mounted on the base, the complementary cylinder having an axis around which the cylinder or roll of gloves is mounted and rotatable, the dispenser being adapted to enable a downstreammost glove on the roll to be manually graspable by a user to detach the fingers of the downstreammost glove from the open bottom end of an immediately upstream glove to the downstreammost glove,
the length of one of the top or bottom sheet being longer than the length of the other of the top or bottom sheet such that a bottommost edge of one of the top or bottom sheet extends beyond a bottommost edge of the other of the top or bottom sheet such that a flap is formed enabling a user to manually separate the top and bottom sheets from each other.

10. The apparatus of claim 9 wherein the second of at least two of the finger receptacles is adapted to receive at least three fingers of a human hand.

11. The apparatus of claim 9 wherein the tip end of the second of at least two of the finger receptacles of the downstream one of the serially attached gloves is readily detachably attached to the bottom proximal edge of the open bottom end of an immediately upstream one of the plurality gloves.

12. The apparatus of claim 9 wherein the complementary cylinder has an axis around which the roll of gloves is mounted and is rotatable such that a downstreammost glove on the roll is manually graspable by a user to to pull the downstreammost glove apart from an immediately upstream attached glove.

13. The apparatus of claim 9 wherein the downstream and upstream gloves are readily detachably attached to each other via a series of adjacent perforations formed in sequential linear or curvilinear arrangement or seam in a sheet of the polymeric material that extends between the distal tip end of the second of the finger receptacles of the downstream glove and the bottom proximal edge of the open bottom end of the upstream glove, the perforations being formed of a size selected to enable ready detachment along the linear or curvilinear arrangement of perforations by exertion of normal pulling force by human hand.

14. The apparatus of claim 9 wherein the sheet of polymeric material comprises a woven or punch formed fabric, a paper material or a solid polymeric material comprised of one or more of polyethylene, polypropylene, polyester or the like and wherein the sheet has a thickness of less than about 500 microns.

15. A method of delivering a series of gloves to a user in serial fashion comprising rotatably mounting a roll of interconnected gloves as claimed in claim 9 on a cylinder in an arrangement wherein a downstreammost glove on the roll is readily manually engageable by a user to pull the downstreammost glove apart from an immediately upstream attached glove.

16. The apparatus of claim 10 wherein the tip end of the second of the at least two finger receptacles of the downstream one of the serially attached gloves is readily detachably attached to the bottom proximal edge of the open bottom end of an immediately upstream one of the plurality gloves.

* * * * *